United States Patent [19]
Gruber

[11] Patent Number: 5,140,855
[45] Date of Patent: Aug. 25, 1992

[54] MONITORING TANK MODULES AND ARRAY FOR USE WITH BIOLOGICAL SENSORS

[75] Inventor: David Gruber, Christiansburg, Va.

[73] Assignee: Biological Monitoring, Inc., Blacksburg, Va.

[21] Appl. No.: 611,653

[22] Filed: Nov. 13, 1990

[51] Int. Cl.$^5$ ............................................. A01K 63/00
[52] U.S. Cl. .................................. 73/432.1; 73/864.91; 73/61.41; 119/3
[58] Field of Search ............... 73/864.91, 863, 863.01, 73/863.02, 863.03, 432.1, 866, 866.5, 53, 61 R, 61.1 R; 324/689, 692, 694, 695, 696; 119/3; 340/573, 620; 435/29, 32, 33

[56] References Cited

U.S. PATENT DOCUMENTS

| | | | |
|---|---|---|---|
| 2,690,158 | 9/1954 | Petty | 119/3 |
| 4,626,992 | 12/1986 | Greaves et al. | 119/3 X |
| 4,723,511 | 2/1988 | Solmon et al. | 119/3 |

FOREIGN PATENT DOCUMENTS

| | | | |
|---|---|---|---|
| 1194627 | 6/1965 | Fed. Rep. of Germany | 119/3 |
| 2083663 | 4/1987 | Japan | 119/3 |
| 3179252 | 7/1988 | Japan | 73/432.1 |
| 3256855 | 10/1988 | Japan | 119/3 |
| 535929 | 2/1977 | U.S.S.R. | 119/3 |
| 971186 | 11/1982 | U.S.S.R. | 119/3 |
| 1109102 | 8/1984 | U.S.S.R. | 119/3 |
| 1302145 | 4/1987 | U.S.S.R. | 73/864.91 |
| 1308306 | 5/1987 | U.S.S.R. | 119/3 |
| 793533 | 1/1988 | U.S.S.R. | 119/3 |

OTHER PUBLICATIONS

*Automated Biomonitoring*, Chapter 2, "An Overview of Automated Biomonitoring-past developments and future needs", pp. 23-39, J. Diamond et al., published in 1988 by Ellis Horwood Limited, Chichester.

Primary Examiner—Tom Noland
Attorney, Agent, or Firm—Staas & Halsey

[57] ABSTRACT

A monitoring tank for fish used as biological sensors wherein water being monitored for quality and toxins continuously flows. Extraneous noise is mostly eliminated by suitable grounding. Aluminum racks with slide guides support the multiple monitorin tanks for each access to the monitoring tanks. The water is discharged from the monitoring tanks into drain trays located under the aluminum racks.

15 Claims, 5 Drawing Sheets

MONITORING TANK MODULES AND ARRAY FOR USE WITH BIOLOGICAL SENSORS

BACKGROUND OF THE INVENTION

1. Field of the Invention

This invention relates to monitoring tanks, modules and an array. The modules contain living organisms, such as fish, while toxicity.

2. Description of the Prior Art

Bio-monitors have been used for assessing water quality, employing living organisms as the sensors. The sensors employed in these systems range from bacteria and invertebrates (such as insects, crustacea, and paramecia) to vertebrates (several species of fish). One sensor of special interest is the ventilatory behavior and activity of fish. This ventilatory behavior or activity can be detected by several methods. One of these methods calls for placing the fish in a monitoring chamber that is electrically insulated, and detecting the microvolts generated by the ventilatory behavior and activity of the fish. The monitoring chamber is exposed to continuous flows of the water being monitored. The electrical signals from a given fish change with the quality or toxicity of the water. The monitoring provides an early warning system, which varies with the application such as whether the monitor is to be used for industrial waste water, municipal waste water discharges, or raw drinking water. The general principles of such a monitoring system are well known, for example, see *Automated Bio-Monitoring* by J. Diamond, M. Collins and D. Gruber, published in 1988 by Ellis Horwood Ltd., Chichester, England, ISBN O 7458-0310-5, and the references cited therein which are incorporated herein by reference.

One of the reasons that fish make good bio-monitors is that they have an extraordinarily good sense of smell. It is estimated by others that a good hunting dog can smell one-thousand times better than his master, and a fish can smell one-thousand times better than a dog. It is further estimated by others that one drop of some chemicals can be placed in Lake Erie, and some fish are so sensitive they can detect it anywhere in the lake.

A fish ventilatory monitoring tank which has been used before consists of a glass tank through which water being monitored can constantly flow, and in which the fish used as the bio-sensor is contained. The tank is insulated and has electrodes at each end of the tank. The tank has a tapered outlet at one end which permits flow over a standpipe for the outlet of the water. The microvolt electrical signals detected by the electrodes are amplified, filtered and processed by a computer.

This old unit of a fish tank upon which the present invention is an improvement, suffers from several problems which include too much electrical noise, the potential for some of the components leaching which would contaminate the water, difficulty of viewing the tanks to examine the fish and ocean the tank, and the lack of an indicator that the water is flowing. The present invention is substantially different and an improvement to the old fish tank or exposure chamber.

SUMMARY OF THE INVENTION

The present invention includes exposure tanks in an array for use with biological sensors such as fish. There are at least two monitoring modules, each containing four tanks which may also be called cells or monitoring chambers. Each module has provisions for automatic water feed and water drainage. The eight monitoring chambers or exposure tanks installed in the two monitoring modules are made of non-leaching electrically insulating material, such as glass, and permit the continuous flow of the water being monitored by the fish. The entire system is well-grounded, and the inlet conduits for the water are preferably made of stainless steel except when flexibility is needed a non-leaching material such as Teflon ® may be used. The exposure tanks (monitoring chambers) are free to individually slide forward to enable inspection, cleaning, etc. Each exposure tank has a visible flow meter which permits adjustment of the flow of the water, and also indicates that water is flowing to the tank.

An arrangement is made for automatically taking a sample of water in an alarm condition. Also, automatic feeding of fish food on a staggered basis is provided so that the fish are fed at different times.

The microvolt electrical signals from the fish are relatively free from any electrical noise by virtue of the improved modules grounded tanks. The microvolt signals are amplified by an appropriate amplifier, filtered and processed by a computer using appropriate software. The amplifier and the software for processing the information are not part of the present invention and are available from Biological Monitoring, Inc., as part of their Bio-Sensor water quality monitoring system (P.O. Box 184, Blacksburg, Va., 24063). They are further described in co-pending U.S. patent applications entitled "BioAmplifier for Sensing the Ventilatory Frequency of Fish", invented by Frank Harrison (filed Nov. 13, 1990, Ser. No. 611,664) and "Method and Apparatus Using threshold Techniques for Generating an Alarm in a Bio-Sensor," invented by M. Kaynor and P. Gradski (filed Nov. 13, 1990, Ser. No. 611,744), which are co-owned by the owner of the present application, and which applications are incorporated herein by reference.

BRIEF DESCRIPTION OF THE DRAWINGS

Various features and advantages of the present invention will be apparent from the following description of a preferred and non-limiting example, and with reference to the accompanying drawings, wherein.

DESCRIPTION OF THE PREFERRED EMBODIMENT

Figure 1:
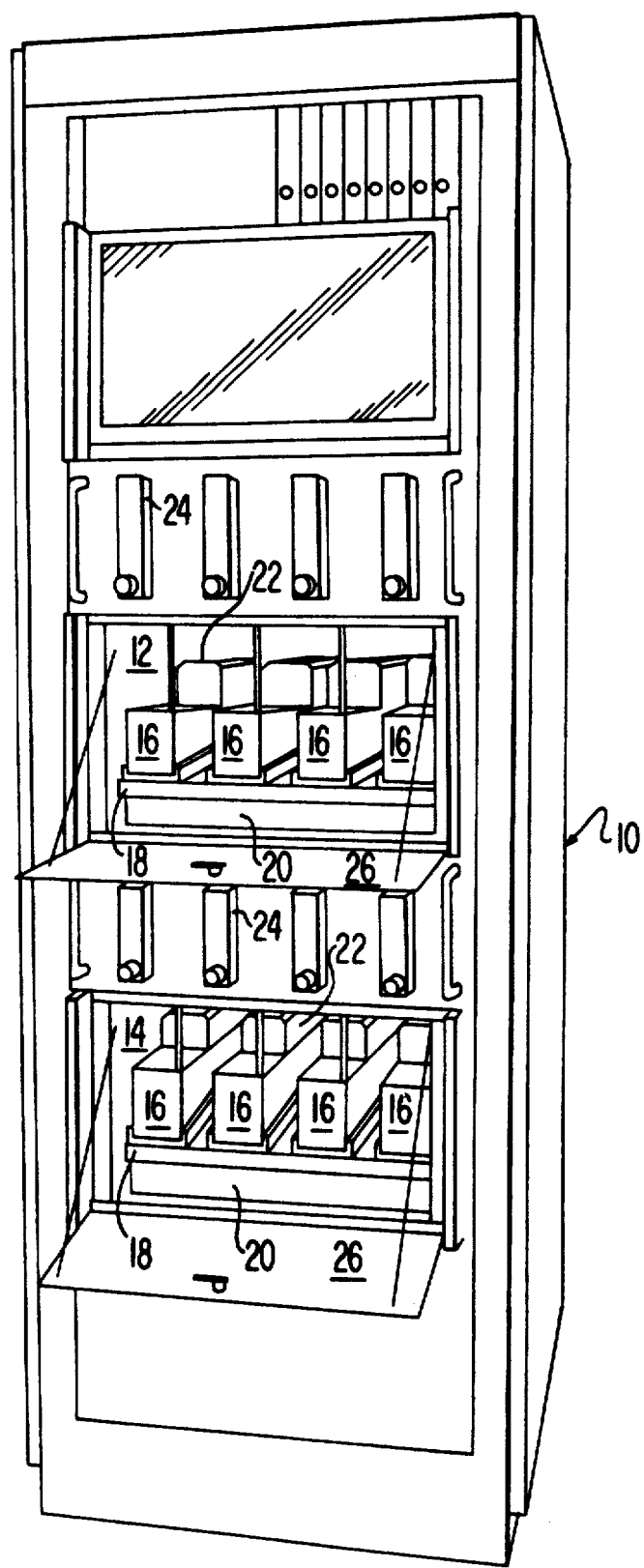
FIG. 1 is perspective view of the exposure modules arranged in a rack.

FIG. 1 is a perspective view of the present invention mounted in a standard 19-inch electronic rack, or housing, 10. There are two monitoring modules 12 and 14, each comprising four monitoring or exposure tanks 16, for containing the fish biological sensors sliding on a rack 18, which is in turn mounted on a drain tray 20. The tanks 16 may also be referred to as chambers or cells. On top of each monitoring chamber 16 is a fish feeder 22, which is an automatic feeding device tank. The preferred feeding device is EHEICHM, which is a naturally slow-feeding battery-operated apparatus that is capable of being programmed on an hourly basis. It is available as model 3580 01, from Hawaiian Marine Imports, Inc., P.O. Box 21687, Houston, Tex., 77218, and is made in West Germany. The feeders are independent and normally feed the fish twice a day. The feeding is staggered so that the fish are fed at different times. When fish are fed it excites them, and they jump around in the water, which causes the readings for that fish to be erratic for a short period of time. Therefore, no two fish are fed at the same time, for example, one may be fed at 7:00, another at 8:00, another at 9:00, etc.

Each tank also has a flow meter 24 which controls the flow rate of the water which is being sampled. This water continuously flows into the tank. The flow meter is a vertical member which contains a valve adjustable by a Knob, and available from a number of manufacturers. The flow meters are readily visible from the front of the rack and indicate that water is in fact flowing to individual tanks. The flow rate is usually set at approximately 2 milliliters per second, with the flow meter having a range from 0 to 4 milliliters per second. The flow meters are rotameters of the floating ball type with integral needle valves. The valves in the intake water manifold are type 316 stainless steel.

Each monitoring module also includes a front door, or panel, 26 that is hinged along its bottom to fold down and make a tray for exposing the individual tanks 16. Normally the door panel is latched in the raised position so that the individual tanks are not visible. The top of the rack or housing 10 contains an amplifier which does not form part of the present invention, but is included in the co-pending patent application supra.

Figure 2:
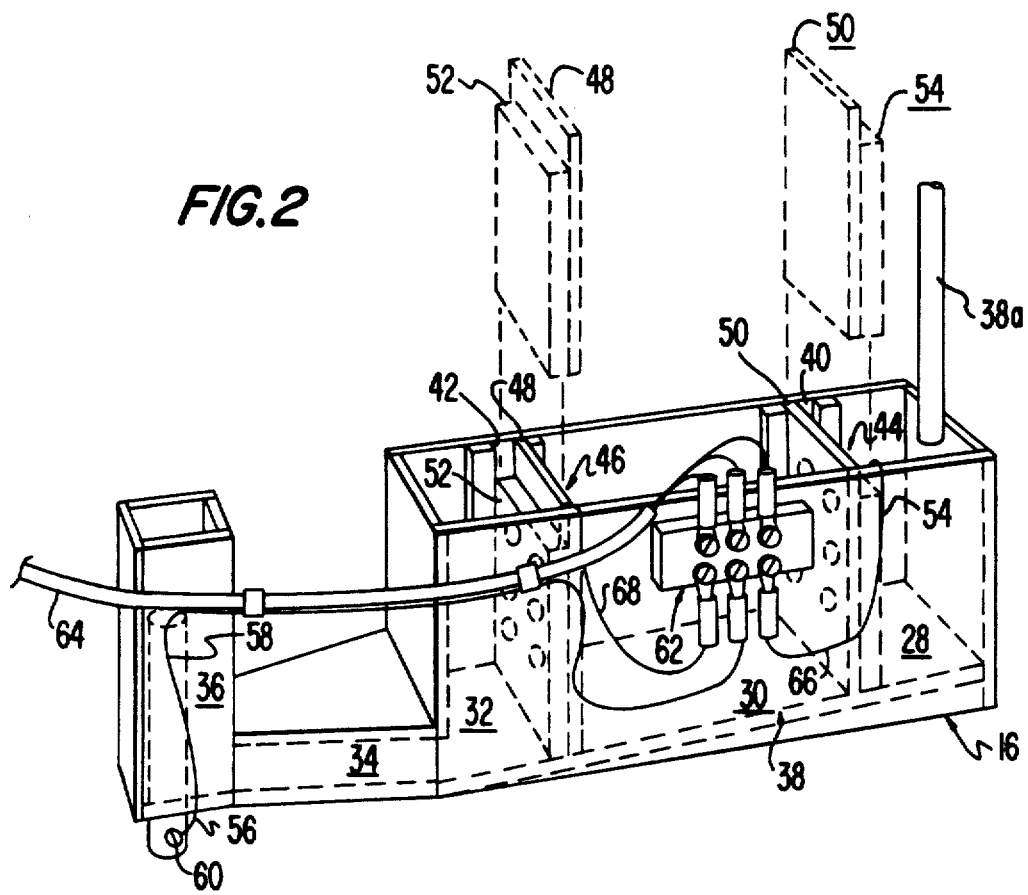
FIG. 2 is a perspective view of an individual exposure tank including the electrical wiring.
Figure 3:
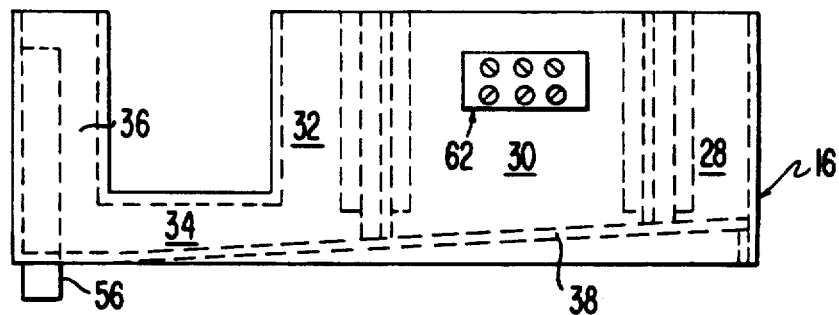
FIG. 3 is side view of the tank of FIG. 2, minus the electrical wiring.
Figure 4:
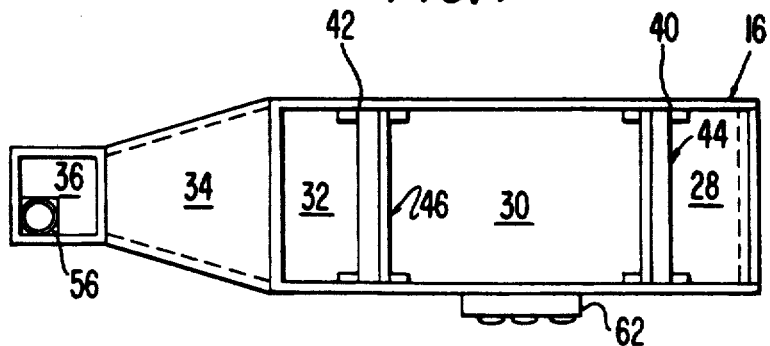
FIG. 4 is a top view of FIG. 3.

With reference to FIGS. 2, 3 and 4, there is shown an individual monitoring tank 16 for containing an individual fish for use as a biological sensor.

The monitoring tanks are approximately 9.75" long, 2.50" wide, and 3.25" tall, and have a volume of approximately 500 milliliters of water. They are constructed of 22 pieces of borosilicate glass and assembled by aquarium-grade silicone rubber adhesive. Thus, the tank is electrically insulated, and the tank material will not dissolve or leach into the water to change its toxicity, or otherwise affect the quality of the water being monitored.

The tank has an inlet section 28, a fish section 30, an outlet section 32, a tapered section 34, and an overflow section 36. The water being sampled is discharged through Teflon ® tubing 38 into inlet section 28, where it flows into fish section 30 and then into outlet section 32. The floor 38 of the tank is sloping.

Slots 40 and 42 ar provided in the side walls of the tank for slidably receiving electrode assemblies 44 and 46. The electrode assemblies may be easily removed for cleaning and replacement. Each electrode assembly comprises a barrier plate 48 and 50, and an electrode plate 52 and 54. Both the barrier plates and the electrode plates have a number of holes passing therethrough, and may have part of the bottom notched. These holes and notches permit the continuous flow of the water being monitored through or around the electrode assemblies. It is desirable that all of the water in the tank continuously be refreshed by new water, so as to avoid any dead spots of water in the tanks. The two barrier plates face the fish section so as to prevent the fish from coming in contact with the electrodes themselves. The electrode plates are mounted on the other side of the barrier plates from the fish section, and use a stainless steel-type 316 20×20 mesh with 0.016 wire diameter stainless steel wire cloth. The wire mesh is attached to the electrode plate with type 316 L size 4 surgical stainless steel wire. The electrode plate is made from ¼" thick virgin Teflon ® material and the barrier plate is made from ⅛" thick virgin Teflon ® material.

The water flow through the tank is approximately 1 liter per minute.

The tapered section 34 is designed so as to enhance the turnover of the water and avoid dead spots.

The standpipe 56 is of type 316 stainless steel and is grounded electrically. This is very important, as water flowing through an insulating type of standpipe or non-grounded outlet will generate electrical noises caused by the turbulence of the water as it drains from the exposure chamber. Since the electrical voltage signals are in the microvolt range, this can be very disturbing to getting good signals from the movement of the fish. A typical signal is 50 microvolts, and is primarily a function of the gill movement. By providing an electrically conducting standpipe that is grounded, this electrical noise has been almost entirely eliminated. The height of the standpipe 56 determines the height of the liquid in the tank as it overflows into the standpipe.

The grounding wire 58 is connected electrically to the standpipe by a screw 60. The other end of the grounding wire is connected to terminal block 62 where it exits through a common ground and cable 64, which goes to the amplifier (not shown), which in turn is grounded to the chassis or other suitable grounding arrangement including the grounding wire in the power cord.

Also connected to terminal block 62 is an electrode mesh wire 66 attached to the electrode mesh on electrode plate 54, and electrode wire 68 attached to the electrode mesh on electrode plate 52. A resistor (not shown) ma be connected at the terminal block between electrode wire 66 and electrode wire 68. Preferably this would be a 10,000 resistor which isolates the positive and negative inputs to the differential amplifier (not shown). Also, the ground wires may be selectively insulated to eliminate any possibilities of ground loops.

Figure 5:
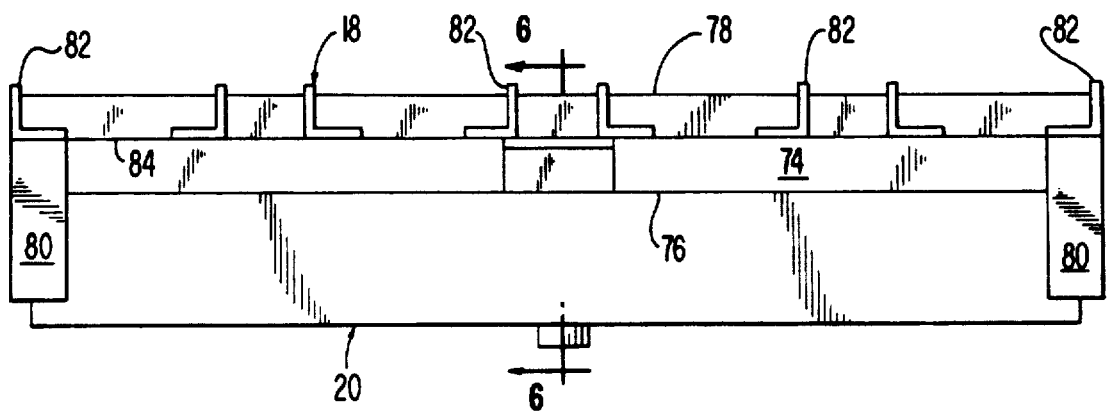
FIG. 5 is a front view of the sliding rack and drain pan of an exposure module containing four tanks.
Figure 6:
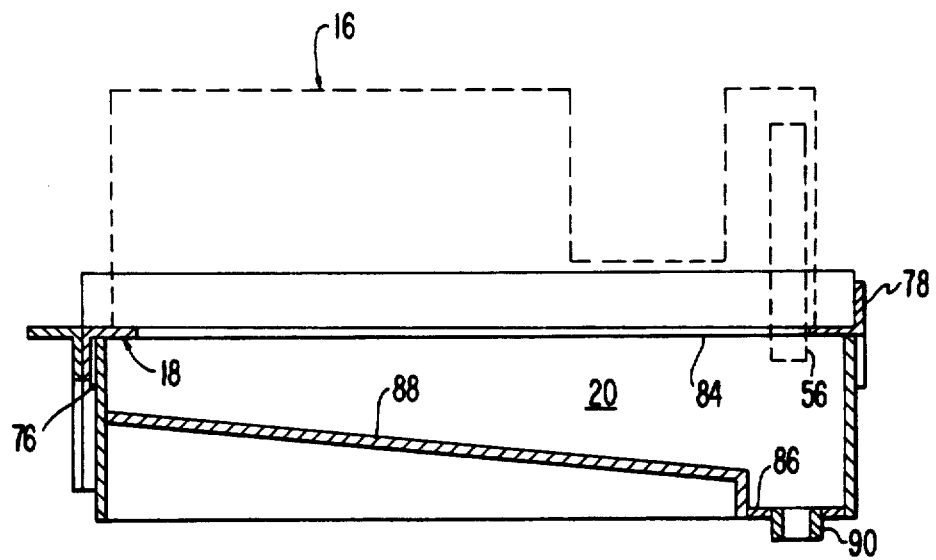
FIG. 6 is a cross-sectional view taken along cross section 6—6 of FIG. 5, and showing by dotted lines a tank in place.
Figure 7:
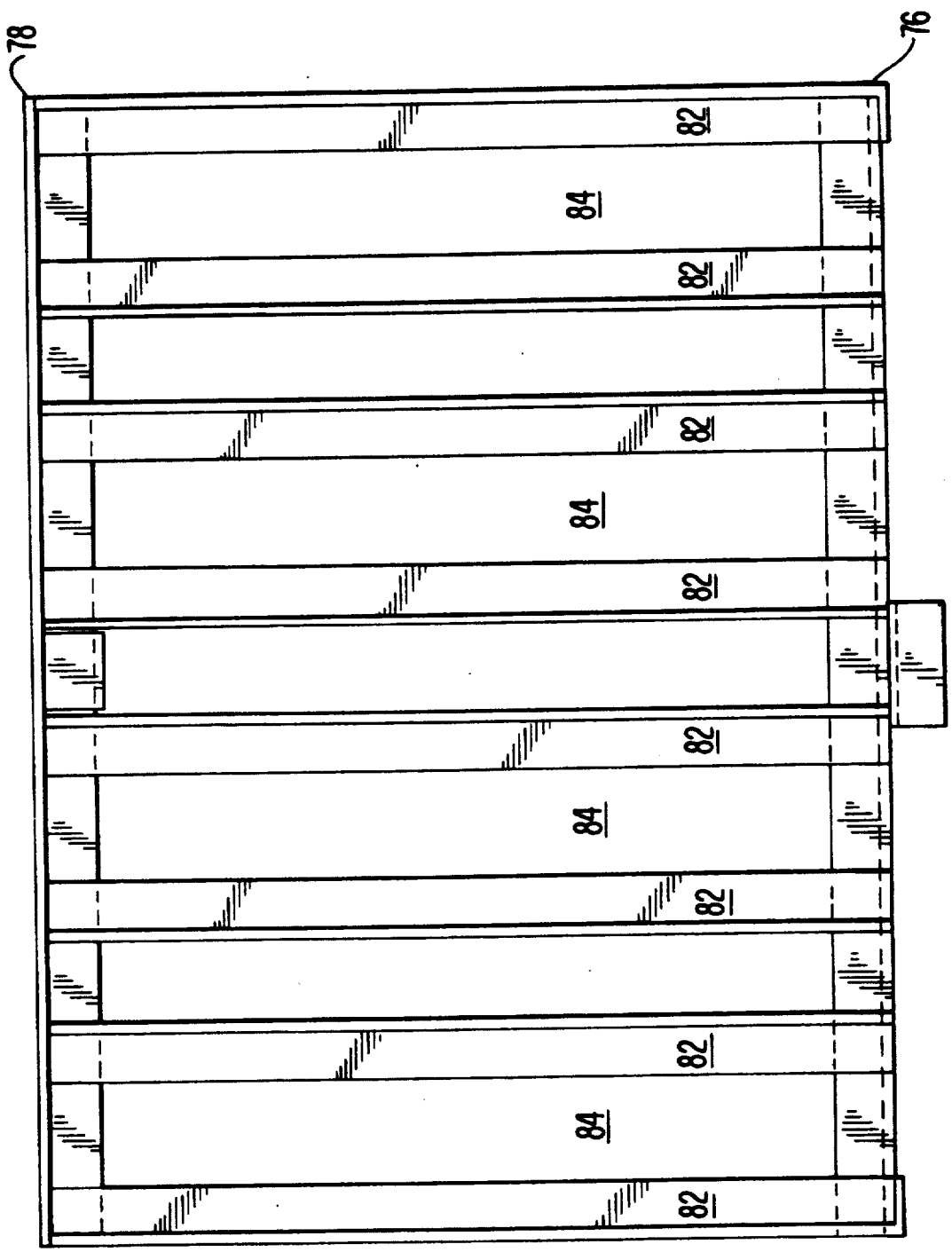
FIG. 7 is a plan view of FIG. 5.

With reference to FIGS. 5, 6 and 7, there is shown an aluminum rack 18 sliding on a plastic drain tray 20. The aluminum rack 18 is made of a number of aluminum angles which are connected together either by welding or similar processes. There is an outer frame 74 surrounding four sides, with the front frame member 76 angled downward, and the rear frame member 78 angled upward. There are two legs 80 at the front of the frame. Mounted in parallel from front to rear on the top of the frame are four pairs of slide guides 82. Each pair of slide guides face one another at a distance to accommodate a monitoring tank being slid fore and aft along the slide guides. There is an opening 84 in the middle between each pair of slide guides so as to accommodate the bottom of standpipe 56. As the water overflows from a tank it exits from the standpipe at the bottom to be discharged into the plastic drain tray 20. This will happen even when the tank is slid to a forward position.

The plastic drain tray 20 is best seen in FIG. 6. The drain tray has a back trough 86 and a sloping bottom 88 leading to the trough. Provided in the trough 86 is a drain 90.

With reference to FIG. 6, the monitoring tank 16 as shown in dotted lines can be slid forward from right to left, or the entire aluminum rack can be slid forward while drain tray 20 remains stationary. The tank can continue to monitor as the water drains from the tank through standpipe 56 into the tray no matter what its position is along the length of the tray. The standpipe slides in the slot openings 84 when it is slid along the surface of aluminum rack 18. The flexible Teflon ® tube 38a through which the continuous flowing water is placed in the monitoring tank is free to bend over any obstructions as the tank is moved or accessed. The fish feeder 22 has been removed for purposes of clarity in all figures except FIG. 1.

Figure 8:
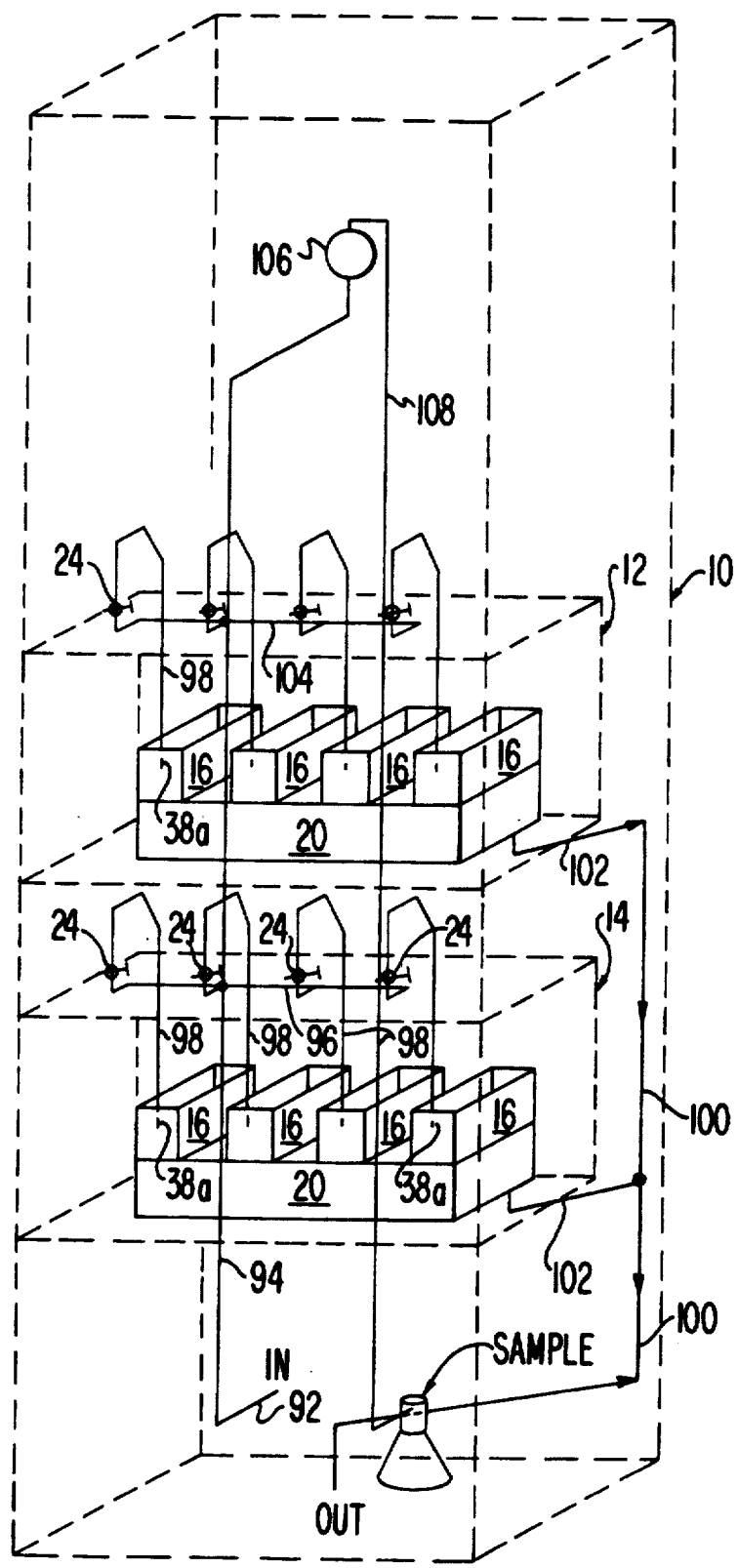
FIG. 8 is a perspective schematic of the plumbing arrangement of FIG. 1.

With reference to FIG. 8, there is shown a perspective schematic of the plumbing system. The water to be sampled comes in through inlet 92 located near the bottom of the rack 10, and proceeds upward through 94 and is connected into manifold 96 of monitoring module 14. The manifold 96 distributes the incoming water to the four flow meters 24 through which it passes and then downward through tube 98. At the bottom end of tube 98, as shown by the dotted lines, is a flexible inert tube 38a, preferably made of Teflon ®, from which the water is discharged into the inlet section 28 of the monitoring tank 16. The water then flows through the monitoring tank 16 and is discharged through the standpipe 56 into the drain dray 20. The discharged water drains onto the drain tray and flows over the sloping bottom 88, where it is collected in trough 86 and exits through drain 90. Drain 90 dumps into common drain pipe 100. The connection between the drain 90 and the common drain pipe 100 is provided by a short length of tubing 102.

The same plumbing system as just explained in connection with monitoring module 12 is provided for monitoring module 14.

The tubing 94 continues above manifold 104 of module 12 to a solenoid valve 106, which is connected to a sample collector tube 108, which dumps into a sample flask 110.

In the event the water being monitored triggers an alarm, such as by exceeding preselected parameters, then the solenoid valve 106 is triggered to open for a predetermined period to allow some of the water which triggered the alarm to be dumped into a sample flask 110. The flask that collects the sample can then be withdrawn, and the water sample collected therein analyzed. A typical flask size would be 500 milliliters, and the flask should preferably be made of an inert material such as glass.

The inlet 92, inlet tubing 94, manifolds 96 and 104, flow meters 24 and associated tubing, and tube 98 are preferably ¼" outside diameter type 316 inch stainless steel which is grounded to the metal chassis. However, an inert material such as Teflon ® tubing is used below the flow meter so that it will be flexible and permitted to bend in being inserted and withdrawn from tank 16. Also, inert material is used to connect the manifolds 96 and 104 as a joint (not shown) between the flow meters. This is a small piece of connecting tubing, and is mainly used for ease and convenience of assembly because the stainless steel tubing is so difficult to work with in tight places. The drainage system is not as critical as to the choice of materials. The plastic used in plastic tray 20, the drain pipe 100 and the short tubing 102 may be made of polyvinyl chloride.

It is important that the materials in the tank 16 not contaminate the water, so the tank must be made from inert materials, preferably borasilicate glass, joined together by a silicone adhesive. The electrode assembly is made from an inert material such as Teflon ®, except for the electrode itself, which is made from stainless steel. The standpipe 56 may be made of a metal conductor, preferably stainless steel, and is grounded. The grounding is by a grounding wire 58, which passes through terminal block 62 into the grounding wire of cable 64, which goes to the amplifier (not shown). The amplifier has a ground wire through its power cord, and the entire rack itself is grounded. This is important in reducing the electrical noise that would otherwise be picked up at the microvolt levels by the electrodes.

The fish usually remain in the tanks an average of six months. One common fish utilized as a sensor is a blue gill. Usually the fish are about 2" in length. When they become larger than 3", they are too big for the small compartment. The unit shown in the embodiment has two monitoring modules 12 and 14, each of which has four monitoring tanks 16. This would be a common unit for on-line monitoring of water quality, with all eight fish being fed the same water sample simultaneously. The system can be modified to have three modules of four tanks each for research and other purposes, for example, one with three modules could have its piping arranged so that each module can operate as a totally separate unit from the other two modules. One example would be have the first module as a control group, a specific toxicant in module two, and a second different toxicant in module three, and observe the actual effects on the fish.

It is important that the materials be chosen so that there is no leaching into the water being tested by the material the water comes into contact with. This is provided for by using stainless steel tubing and inert plastic such as Teflon ®.

It is thus seen that an exposure module and array for use with biological sensors such as fish has been provided which permits ease of cleaning of the electrodes, a reduction of electrical noise so that the microvoltage signals can be substantially noise-free, and the entire unit can be easily utilized and more easily maintained as an automated monitoring array of tanks.

Although the present invention has been described and illustrated with respect to a preferred embodiment thereof, it is to be understood that various changes and modifications will be apparent to those skilled in the art, and may be made without departing from the scope of the present invention as defined in the following claims.

What is claimed is:

1. A biological monitoring tank comprising:
    an electrically insulated tank made of non-leaching materials having an inlet area for receiving water to be monitored at one end, and an outlet for said water at the other end;
    containing area for containing a biological sensor located in said tank between said one end and said outlet;
    a first electrode in said tank located between said containing area and said one end;
    a second electrode in said tank located between said containing area and said outlet;
    an electrically conducting standpipe made of non-leaching material located in said electrically insulated tank at said outlet for controlling the depth of said water in said tank and discharging any overflow; and an electrical grounding connection attached to said standpipe for electrical grounding of said standpipe.

2. The biological monitoring tank of claim 1, wherein a pair of slots is provided in said tank for both said first electrode and said second electrode; and said first and second electrodes each consisting of a flat barrier facing the containing area and an electrically conducting electrode on an outboard side of said barrier and thus facing away from said containing area, said barriers and said electrodes being adapted to slide in a removable manner in said slots.

3. The biological monitoring tank of claim 2, wherein each of said barriers is perforated to permit the water being monitored to pass therethrough on a continuous basis, and said electrode being made of a stainless steel mesh carried on a non-leaching insulating flat plate.

4. The biological monitoring tank of claim 2, wherein there is included:

a drain pan having an outlet spout;

a slide mounted on said drain pan to carry said tank and permit it to slide over said drain pan in a manner that its outlet is constantly over said drain pan as it slides thereover; and a flexible tubing made of non-leaching material arranged to be inserted in said inlet area and flexibly moved therefrom.

5. A biological monitoring tank as set forth in claim 4, wherein there are provided at least two tanks and two drain pans; and a common drain into which both of said drain pans drain their contents.

6. A biological monitoring tank as set forth in claim 5, wherein said flexible tube is connected to a visible flow meter and valve for adjusting the amount of flow of water to be monitored and indicating that such water is flowing.

7. A biological monitoring tank as set forth in claim 6, wherein said water to be monitored is connected to a powered valve;

a sampling container of non-leaching materials; and a tubing connecting said powered valve to said sampling container whereby, upon said powered valve being actuated, a measured flow of water to be monitored is conducted to said sampling container.

8. A biological monitoring tank as set forth in claim 7, wherein said powered valve is powered by an electrical solenoid.

9. A biological monitoring tank as set forth in claim 8, wherein said drain pan has a bottom which slopes to one side thereof and contains a trough at a low end of said sloping bottom.

10. The biological monitoring tank of claim 1, wherein there is included:

a drain pan having an outlet spout;

a slide mounted on said drain pan to carry said tank and permit it to slide over said drain pan in a manner such that its outlet is constantly over said drain pan as it slides thereover; and a flexible tubing made of non-leaching material arranged to be inserted in said inlet area and flexibly moved therefrom.

11. The biological monitoring tank of claim 10, wherein said drain pan has a bottom which slopes to one side thereof and contains a trough at a low end of said sloping bottom.

12. The biological monitoring tank of claim 11, wherein there are provided at least two tanks and two drain pans; and a common drain into which both of said drain pans drain their contents.

13. The biological monitoring tank of claim 10, wherein said flexible tube is connected to a visible flow meter and valve for adjusting the amount of flow of water to be monitored and indicating that such water is flowing.

14. The biological monitoring tank of claim 13, wherein said water to be monitored is connected to a powered valve;

a sampling container of non-leaching materials; and a tubing connecting said powered valve to said sampling container whereby, upon said powered valve being actuated, a measured flow of water to be monitored is conducted to said sampling container.

15. The biological monitoring tank of claim 14, wherein said powered valve is powered by an electrical solenoid.

* * * * *